United States Patent
Carter

(10) Patent No.: US 8,209,825 B2
(45) Date of Patent: Jul. 3, 2012

(54) SYSTEM FOR QUICK RELEASE

(76) Inventor: Paul Carter, Fayatteville, NC (US)

( * ) Notice: Subject to any disclaimer, the term of this patent is extended or adjusted under 35 U.S.C. 154(b) by 0 days.

(21) Appl. No.: 13/370,890

(22) Filed: Feb. 10, 2012

(65) Prior Publication Data
US 2012/0124785 A1    May 24, 2012

Related U.S. Application Data

(63) Continuation of application No. 12/994,135, filed as application No. PCT/US2009/044950 on May 22, 2009.

(60) Provisional application No. 61/055,267, filed on May 22, 2008.

(51) Int. Cl.
*A44B 11/00* (2006.01)
*A44B 11/25* (2006.01)

(52) U.S. Cl. ............. 24/634; 24/606; 24/614; 24/615; 24/616

(58) Field of Classification Search .......... 24/165, 24/200, 265 BC, 614, 615, 616, 617, 603, 24/606, 621, 625, 630, 631, 633, 634, 637, 24/640, 647, 664, 666; 224/271; 2/102; 182/3; 403/322.1
See application file for complete search history.

(56) References Cited

U.S. PATENT DOCUMENTS

| 6,487,761 | B2 * | 12/2002 | Van Tassel | 24/606 |
| 6,955,138 | B2 * | 10/2005 | DeBien | 119/776 |
| 7,162,978 | B2 * | 1/2007 | Debien | 119/772 |
| 7,640,639 | B2 * | 1/2010 | de Bien | 24/615 |
| 7,814,567 | B2 | 10/2010 | Dovner et al. | |
| 7,954,211 | B2 * | 6/2011 | De Bien | 24/606 |
| 7,987,523 | B2 | 8/2011 | Cole et al. | |
| 2002/0092140 | A1 * | 7/2002 | Van Tassel | 24/614 |
| 2009/0282595 | A1 | 11/2009 | Branson et al. | |

* cited by examiner

*Primary Examiner* — Robert J Sandy
*Assistant Examiner* — Louis Mercado
(74) *Attorney, Agent, or Firm* — Kilpatrick, Townsend & Stockton, LLP.

(57) ABSTRACT

Release assembly for a personal equipment carrier. Release assembly includes securing component, a plurality of first cable assemblies, a plurality of attachment assembly first portions, trigger termination, and trigger activator. Securing component is attachable to a personal equipment carrier. The first cable assemblies, include an outer member and an inner member. A first end of each first cable assembly outer member is anchored to the securing component. Each attachment assembly first portion includes a detachment portion. The detachment portion is attached to a second end of each first cable assembly inner member. The detachment portion is operable, upon tensioning of the attached first cable assembly inner member, for detaching the attachment assembly first portion from an attached attachment assembly second portion. The trigger termination is connected to the first end of each first cable assembly inner member at the securing component. The trigger activator is connected to the trigger termination.

1 Claim, 4 Drawing Sheets

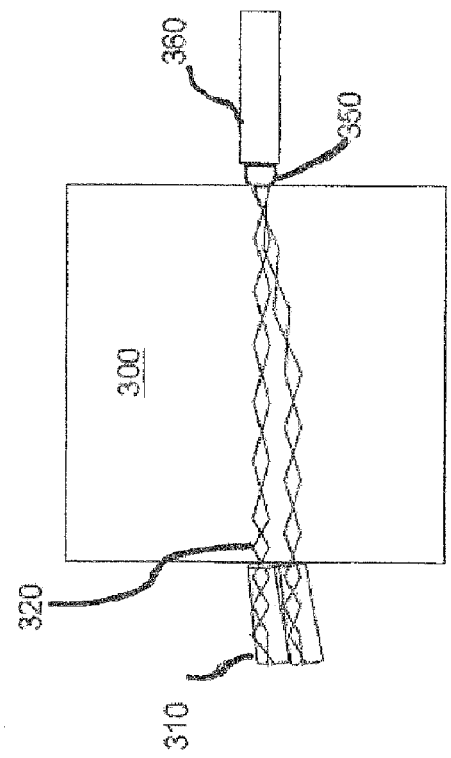
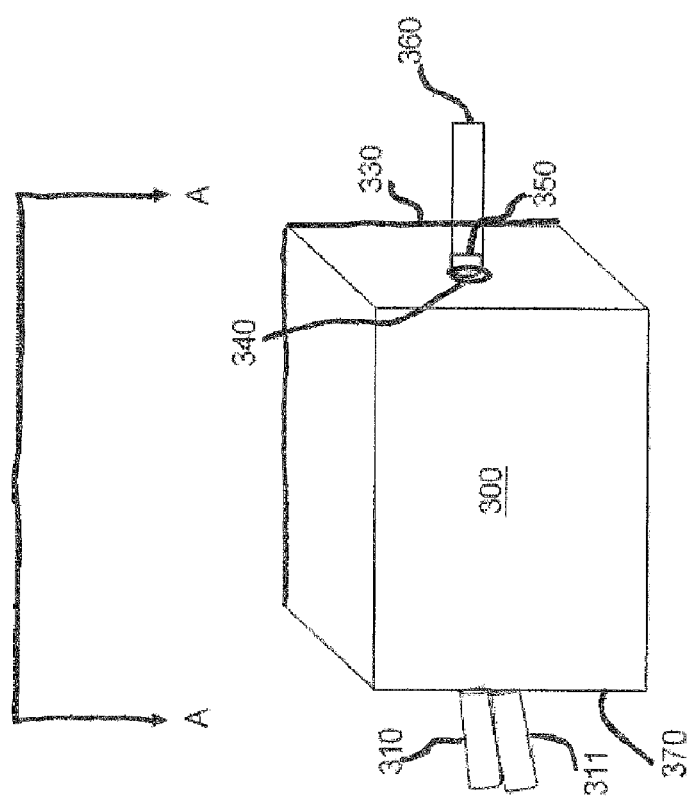

SYSTEM FOR QUICK RELEASE

CROSS-REFERENCE TO RELATED APPLICATIONS

The present application is a continuation of prior U.S. patent application Ser. No. 12/994,135 filed Jun. 21, 2011; which is the national stage entry of PCT/US09/44950, filed May 22, 2009; which claims the benefit of priority to U.S. Provisional Pat. App. Ser. No. 61/055,267, filed May 22, 2008.

BACKGROUND OF THE INVENTION

The present technology relates to a remote release assembly for use with one or more attachment assemblies. More particularly, the technology relates to a system and method of detaching one or more attachment assemblies from a single, remotely-located release assembly with trigger.

Currently, soldiers are issued large quantities of equipment to increase lethality, survivability, mobility and/or target acquisition capabilities. Often, little consideration is given to item deployment, storage, transport and/or utilization. A soldier can therefore find himself forced to place items in hard-to-reach locations when securing issued equipment to his person. This can lead to inefficiencies in both carrying equipment and accessing equipment for use. Without the ability to quickly detach necessary items from a soldier's person, a soldier's life can be unnecessarily endangered. Moreover, detached items must be easily reattached. A system and method of attaching and quickly detaching multiple pieces of equipment to a soldier is, therefore, required.

SUMMARY OF THE INVENTION

Accordingly, the present technology has been achieved to solve the above problems and carry out a further improvement. The present technology discloses a system and method of attaching and quickly detaching a number of items comprising: a remote release enclosure having a connection side and a trigger side, at least one cable assembly traversing through the release enclosure from the connection side to the trigger side, a trigger assembly coupled the at other end one cable assembly, and a plurality of attachment assemblies coupled at least one cable assembly. Embodiments of the release assembly include securing component, a plurality of first cable assemblies, a plurality of attachment assembly first portions, trigger termination, and trigger activator. Securing component can be attachable to a personal equipment carrier. The first cable assemblies, can include an outer member and an inner member. A first end of each first cable assembly outer member can be anchored to the securing component. Each attachment assembly first portion can include a detachment portion. The detachment portion can be attached to a second end of each first cable assembly inner member. The detachment portion can be operable, upon tensioning of the attached first cable assembly inner member, for detaching the attachment assembly first portion from an attached attachment assembly second portion. The trigger termination can be connected to the first end of each first cable assembly inner member at the securing component. The trigger activator can be connected to the trigger termination.

BRIEF DESCRIPTION OF THE DRAWINGS

FIG. 3A is a perspective view of a remote trigger assembly for quick release in accordance with an exemplary embodiment;

FIG. 3B is a cross-sectional view along axis A-A of the remote trigger assembly for the system for quick release depicted in FIG. 3A in accordance with an exemplary embodiment.

DETAILED DESCRIPTION

Reference will now be made in detail to embodiments of the technology. Each example is provided by way of explanation of the technology only, not as a limitation the technology. It will be apparent to those skilled in the art that various modifications variations can be made in the present technology without departing from the scope or spirit of the technology. For instance, features described as part of one embodiment can be used on another embodiment to a still further embodiment. Thus, it is intended that the present technology cover such modifications and variations that come within the scope of the technology.

Figure 1:
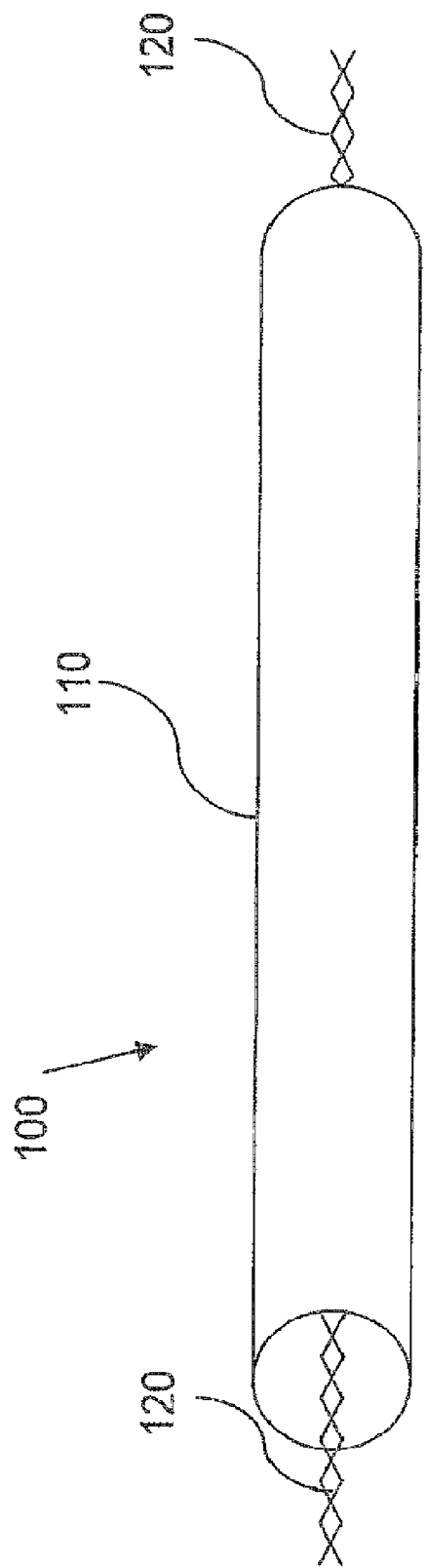
FIG. 1 is a perspective view of a cable assembly for the system for quick release accordance with an exemplary embodiment.

As is shown in FIG. 1, an embodiment of the present technology comprises at least one cable assembly 100. The at least one cable assembly can comprise an outer shell 110 and can a plurality of inner 120 or wires running coaxially therewithin. The outer shell 110 can of any shape known in the art. For example, outer shell 110 can be cylindrical, triangular, rectangular, or any other similar shape. Alternatively, the outer shell 110 can also be a hollow outer wire. Each of the plurality inner cables 120 or can consist of two or more members. The members can be strands, cables, or wires that are braided, entwined, or wrapped. The outer shell 110 and/or the plurality inner cables 120 can be made of a flexible material with little stretch. For example, the outer shell 110 and/or inner cables 120 can be made of bungee cord, elastic cord, nylon cord, or any other similar flexible material. With flexible material having little stretch, it is well known that as the diameter of each inner cable 120 increases, the resistance required to tension each inner wire will increase. The length of the cable assembly 100 can vary depending on the required use, and this variance can also affect the resistance required to tension the inner cable 120.

Figure 2B:
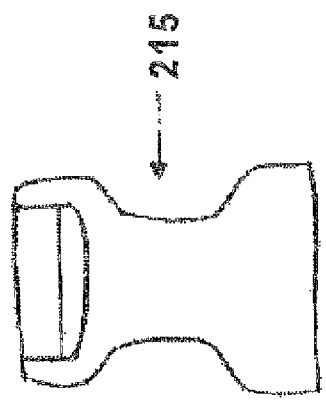
FIG. 2B is a frontal view of a female portion of an attachment assembly the system for quick release in accordance with an exemplary embodiment.
Figure 2A:
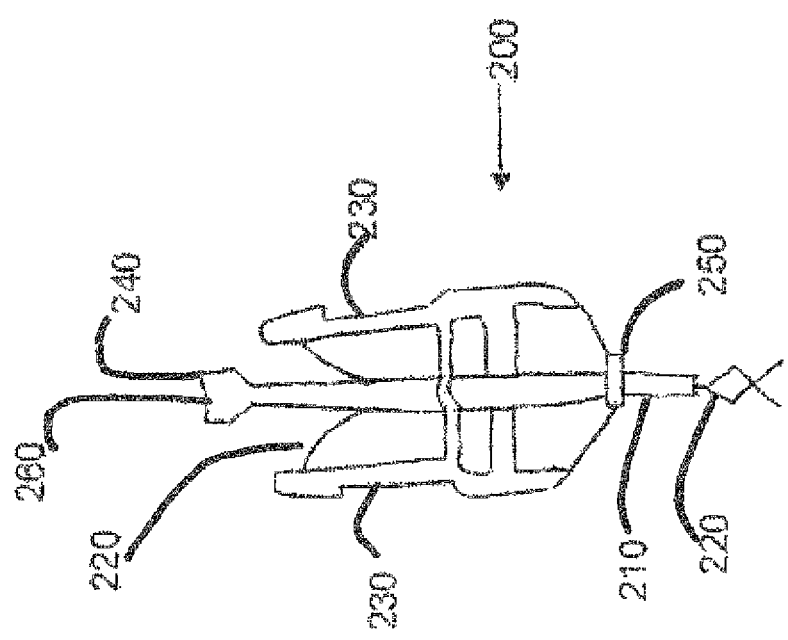
FIG. 2A is a frontal of a male portion of an attachment assembly for the system for quick release in accordance with an exemplary embodiment.

As is shown in FIGS. 2A and 2B, an exemplary embodiment of the present technology comprises an attachment assembly which can be used for the attachment of utility items to a larger platform. The attachment assembly can comprise a male portion 200 and a female portion 215, both of which can be configured for mating engagement with each other. For example, the male portion 200 and the female portion 215 can be configured such that they can be locked, attached, inserted, buckled or fit together to form a single unit. The attachment assembly can be a side-release buckle, a side buckle, a snap buckle, an end release buckle, or any other similar attachment assembly as is known in the art. Both the male portion 200 and female portion 215 can be made a number of materials including, but not limited to, metals and plastics depending on the required use. For example, the attachment assembly illustrated in FIGS. 2A and 2B has a male portion having an inner guide post 240 between two outer guide posts 230 and a female portion 215 having apertures for matingly engaging the inner guide post 240 and outer guide posts 230 of the male portion 200. When the female portion 215 and male portion 200 of the attachment assembly shown in FIGS. 2A and 2B engage, the guide post 240 and outer guide posts 230 snap, secure, or fasten in place with the apertures of the female portion 215.

The male portion 200 can comprises an inner guide post 240 between at least two outer guide posts 230. The outer shell 210 of the cable assembly (See FIG. 1, 100) can coupled to the proximal end 250 of male portion 200 of a corresponding attachment assembly, while at least one of plurality of inner cables extends transversely through the inner guide post 240 of the corresponding attachment assembly towards the distal end 260 of the male portion 200. Alternatively, the outer shell 210 of the cable assembly can be anchored to the proximal end of the male portion 200 of a corresponding attachment assembly. Each of the plurality of inner cables 220 can have at least two members, such as attachment portions, braided cords, two entwined cords, or any other types members. As illustrated in FIG. 2A, the two attachment portions of each of the plurality of inner cables 220 can be configured that one of the attachment portions couples to the outer guide post 230 located to the right side of the inner guide post 240, and a second one of the attachment portions couples to the outer guide post 230 located to the left side of the inner guide post 240. For example, one of the braided cords of one of the plurality of inner cables 220 can extend from the inner guide post 240 and attach to an inner wall of one of the outer guide posts 230. In at least some embodiments, one of the plurality of inner cables 220 extends through the inner guide post 230 of at least one of the respective male portions 200, and at least two of the braids of the one of the plurality of inner cables 220 exit the inner guide post 240 and are coupled to an outer guide post 230 located on opposite sides of the inner guide post 240.

When one of the plurality of inner cables 220 is tensioned, the outer guide posts 230 can move closer to or approach the inner guide post 240 based upon the above couplings of the inner cable 220 to the outer guide posts 230. Consequently, the male portion 200 can be disengaged or unlocked from the female portion 215. In one exemplary embodiment, the outer guide posts 230 can be manually squeezed or moved closer to the inner guide post 240, allowing a release of the male portion 200 from the female portion 215. In another examplary embodiment, the outer guide posts 230 can be moved closer to or approach the inner guide 240 by a trigger as win be described later on the disclosure.

Figure 4:
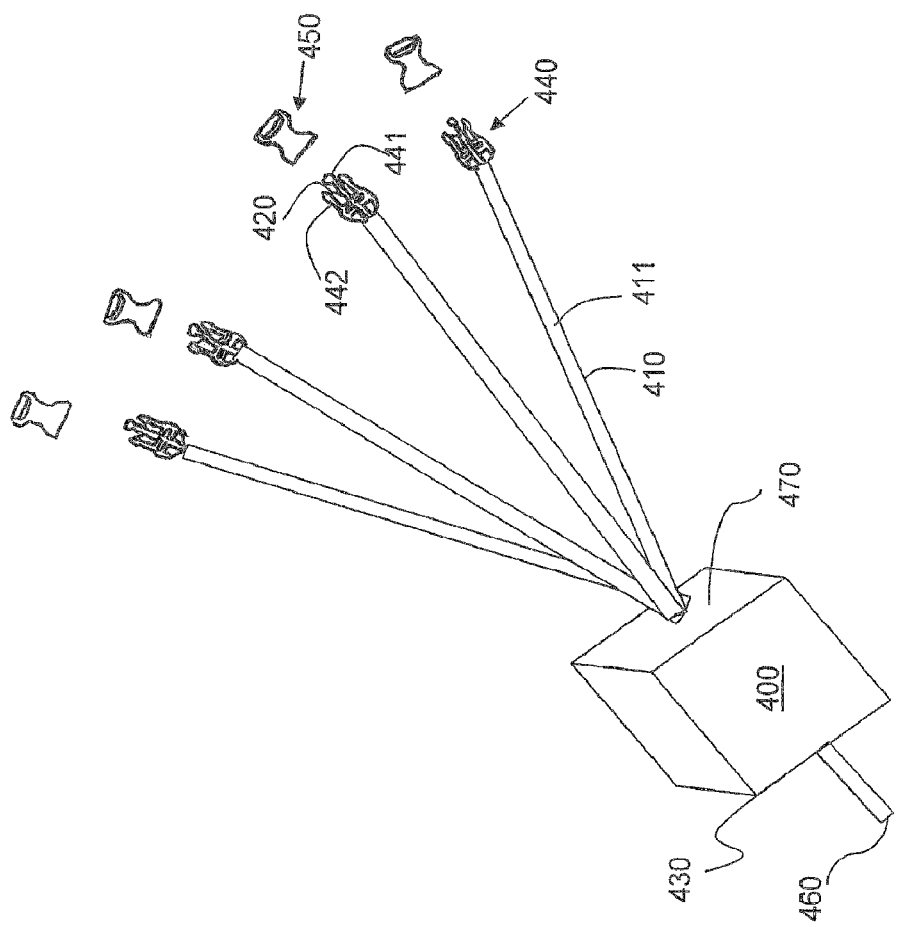
FIG. 4 is a perspective view of a system for quick release in accordance with an exemplary embodiment.

FIGS. 3A, and 3B and 4 show an example embodiment of the current technology comprising a remote release assembly. The remote release assembly can comprise a remote release assembly enclosure at least one assembly 310, a trigger assembly 360, and a plurality of attachment assemblies 440, 450. The remote release assembly enclosure can be, but is not limited to, a housing, a box, an enclosure, or a receptacle having any number sides defining an area. The remote release assembly enclosure 300 can be made of any material known in the including, but not limited metals or plastics. The remote release assembly enclosure 300 can be covered or wrapped in a material compatible with Modular Lightweight Load-carrying Equipment (MOLLE) standard. The remote release assembly enclosure 300 can be attached to a person in any way in the art, including, but not limited to: Velcro, dips, adhesive, straps, buttons, MOLLE, and ties.

The remote release assembly enclosure 300 can have a connection side 370 and a trigger side 330. Though the trigger side 330 and connection side 370 are shown on opposite ends of the remote release assembly enclosure 300, it should be appreciated that the trigger side 330 and connection side 370 can be located on any side of the remote release assembly enclosure 300, including on the same side. At least one cable assembly 311 can be coupled to the remote release assembly. As depicted in FIGS. 3A and 3B, the at least one cable assembly 311 can traverse through the remote release enclosure 300 from the connection side 370 to the trigger side 330. The at least one cable assembly 311 can be anchored to the connection side 370 of the remote release enclosure 300 using any method known in the art. It should be appreciated that two cable assemblies 311 are shown, but there can be any number of cable assemblies 311 attached to the remote release assembly enclosure 300.

The at least one cable assembly 311 can be a cable assembly as described in the previous examples. The remote release assembly is described with respect to a cable assembly as described above comprising an outer shell 310 and a plurality of inner cables 320. Referring to FIGS. 3A and 3B, the outer shell 310 of the cable assembly 311 can be anchored to the connection side 370 of the remote release enclosure 300 The of inner cables 320 can traverse through the remote release enclosure 300 from the connection side to the trigger side 330 The plurality of inner cables 320 can enter the remote release enclosure 300 at the connection-side aperture show) and can pass through the trigger-side aperture 340 to terminate at the trigger side 330 The ends of each of the plurality of inner cables 320 that are proximal to the trigger side 330 the remote release enclosure 300 can terminate at the trigger assembly 360.

The trigger assembly 360 can include a trigger handle 350. The trigger handle 350 can comprise a ring, wherein at least one of the plurality of inner cables 320 terminates at the curved surface of the ring. FIGS. 3A and 3B illustrate a D-Ring exemplary purposes, but persons of ordinary skill in the art will appreciate that the trigger handle can be coupled to the plurality of inner cables 320 by other attachments, such as ties, circular rings, clips, or any other types of attachments known in the art. The flat side of the trigger handle 350 can anchor trigger assembly 360 to the remote release enclosure 300, also referred to herein as a securing component. The trigger assembly 360 can be made of any material in the art, including, but not limited to a MOLLE-compatible material, nylon webbing, cloth, metal, or plastic. The trigger assembly 360 should be of a size able to be gripped by the user, but can be of any useful length. The trigger assembly 360 can be removably coupled to the at least one cable assembly, such that the trigger 350 can be removed and replaced with a different trigger handle 350 as required or dependent upon user preference. It should be noted that a stopper (not shown) can be attached to both the trigger handle 350 and the connection side 370 to prevent the over-extension of any of the plurality of inner cables 320. The stopper (not shown) can be made of cloth, metal, plastic or any other appropriate material and can be of a length appropriate to prevent the at least one inner wire 320 from extending past a pre-determined point. The stopper can be coupled to the trigger assembly 360 and to the connection side 370 or to the trigger side 330 of the remote release enclosure 300.

The plurality of attachment assemblies (not pictured in FIGS. 3A and 3B) can each be coupled to an opposite end of a respective cable assembly 310. The coupling of the attachment assemblies and the respective cable assembly 310 can operatively couple the attachment assembly to the trigger assembly 360. The attachment assemblies can. be a side buckle, a side release buckle, and end release buckle, a snap buckle, or any other similar attachment assembly. For example, an attachment assembly having a male portion and a female portion, such as the attachment assembly described above, is coupled to the trigger assembly 360, the trigger assembly 360 can be actuated to release or release the male portion from female portion. For example, when the trigger 350 is activated, the movement of the trigger assembly 360 can transferred to each of the plurality of attachment assemblies such that at least a portion of the outer guide posts of the male portions approaches inner guide posts each of the plurality of attachment assemblies. The coupling of the attachment assembly its respective cable assembly 310 is described in more detail below.

FIG. 4 shows an example embodiment wherein multiple cable assemblies 410 can be activated from a single, remote trigger assembly 400. While four cable assemblies 410 are shown, it should be appreciated that any number of cable assemblies 410 can be activated from a single, remote trigger assembly 400. The cable assemblies 410 can be attached to connection side 470 of the remote trigger assembly 400. The trigger 460 can be located on the trigger side 430 of the remote release enclosure 400. The male portion 440 of the attachment assembly can be secured, fixed, or attached to the female portion 450 of the attachment assembly. Each of the plurality of inner cables 420 of each cable assembly 410 can run from outer guide posts 442 of the male portion of the corresponding attachment assembly 440, through the inner guide post 441, transversely through the outer shell 411 of the cable assembly 410, through a connection-side aperture (not shown) in the remote trigger assembly 400, through a trigger side aperture (not shown) in the remote trigger assembly 400, and can finally terminate at or affix to the trigger handle shown), which is further connected to the trigger assembly 460. Such a coupling permits movement of the trigger assembly 460 to transfer to each of the plurality of attachment assemblies 440, 450, whereby at least a portion of each of the outer guide posts 442 of each of the plurality of attachment assemblies approaches each of the inner guide posts 441 of each of the plurality of attachment assemblies. For example, pulling, tensioning, twisting or activating the trigger 460 of the remote trigger assembly 400 can retract the plurality of inner cables 420 the cable assemblies 410, which can retract the outer guide posts 442 on the male portions 440 of the attachment assemblies. Consequently, the male portion 440 of the attachment assembly can be disengaged or released from the female portion 450. It should be appreciated that male portion 440 can be disengaged manually from respective female portion 450 of an attachment assembly by squeezing or pressing the outer guide posts 442 towards inner guide post 441.

The remote release assembly described herein can be configured with a backpack, belt, or other utility harness worn by a user. The remote release assembly can attached to a backpack, belt, or other utility harness by attaching the remote release enclosure 400 via a clip, ties, adhesive, threads, or any other attachment. The user can attach equipment, such as a water bottle, compass, or other types equipment to a respective female portion 450 an attachment assembly. The equipment can then be attached or secured to the backpack, belt, or other utility harness by engaging, snapping, or securing the female portion 450 to the corresponding male portion 440 of the attachment assembly. When the user desires to remove or release the equipment from the backpack or belt, the outer guide 440 can be manually squeezed or pressed towards the inner guide post of the attachment assembly corresponding to the individual piece of equipment. Alternatively, if the user desires to remove or release all pieces of equipment from the backpack or belt, the trigger assembly 460 can be actuated which transfers movement of the trigger assembly 460 to the plurality of attachment assemblies, whereby at least a portion of each of the outer guide posts 442 of each the plurality of attachment assemblies approaches each of the inner guide posts 441 of each of the plurality attachment assemblies. For example, pulling, tensioning, twisting or activating the trigger 460 of the remote trigger assembly 400 can retract the plurality of inner cables 420 of the cable assemblies 410, which can retract the outer guide posts 442 on the male portions 440 the attachment assemblies. Consequently, the male portion 440 of the attachment assembly can be disengaged or released from the female portion 450, which releases each piece of equipment from the backpack or belt to which the remote release enclosure 400 is attached.

Exemplary embodiments have been described hereinabove regarding the implementation of the remote release assembly on a carrying device, such as a backpack. However, one of ordinary skill in the art will appreciate that this disclosure relates to a system and method for quick release. Various modifications to and departures from the disclosed embodiments will occur to those having skill in the art. The subject matter that is intended to be within the spirit of this disclosure is set forth in the following claims.

What is claimed is:

1. A release assembly for a personal equipment carrier, the release assembly comprising:
    a securing component attachable to a personal equipment carrier;
    a plurality of first cable assemblies,
    each first cable assembly comprising an outer member and an inner member, and
    a first end of each first cable assembly outer member anchored to the securing component;
    a plurality of attachment assembly first portions,
    each attachment assembly first portion comprising a detachment portion, the detachment portion:
    attached to a second end of each first cable assembly inner member, and
    operable, upon tensioning of the attached first cable assembly inner member, for detaching the attachment assembly first portion from an attached attachment assembly second portion; and
    a trigger termination, connected to a first end of each first cable assembly inner member at the securing component, and
    a trigger activator connected to the trigger termination, the trigger activator operating to tension each first cable assembly inner member to detach the attachment assembly first portion from the respective second portion attached attachment assembly.

\* \* \* \* \*